US008481011B2

(12) United States Patent
Bordat et al.

(10) Patent No.: US 8,481,011 B2
(45) Date of Patent: Jul. 9, 2013

(54) USE OF POLYUNSATURATED COMPOUNDS AS WHITENING AGENTS

(75) Inventors: Pascal Bordat, Mervilla (FR); Roger Tarroux, Toulouse (FR); Jean-Hilaire Saurat, Geneva (CH); Olivier Sorg, Geneva (CH); Sylvie Daunes-Marion, Toulouse (FR)

(73) Assignee: Pierre Fabre Dermo-Cosmetique, Boulogne-Billancourt (FR)

( * ) Notice: Subject to any disclaimer, the term of this patent is extended or adjusted under 35 U.S.C. 154(b) by 430 days.

(21) Appl. No.: 12/086,596

(22) PCT Filed: Dec. 14, 2006

(86) PCT No.: PCT/EP2006/069729
§ 371 (c)(1),
(2), (4) Date: Oct. 28, 2008

(87) PCT Pub. No.: WO2007/068743
PCT Pub. Date: Jun. 21, 2007

(65) Prior Publication Data
US 2009/0304614 A1  Dec. 10, 2009

(30) Foreign Application Priority Data

Dec. 14, 2005 (FR) ..................... 05 12660

(51) Int. Cl.
*A61Q 5/08* (2006.01)
(52) U.S. Cl.
USPC ............. 424/62; 424/401; 514/690; 514/723; 514/729
(58) Field of Classification Search
USPC ................ 424/62, 401; 514/690, 723, 729
See application file for complete search history.

(56) References Cited

U.S. PATENT DOCUMENTS

| 5,192,544 | A | * | 3/1993 | Grollier et al. ............. 424/401 |
| 5,447,716 | A | * | 9/1995 | LaGrange .................... 424/62 |
| 5,786,391 | A | * | 7/1998 | Gudas et al. ................ 514/640 |
| 5,962,534 | A |   | 10/1999 | Gudas et al. |
| 6,190,664 | B1 | * | 2/2001 | Dampeirou ................. 424/736 |
| 6,365,135 | B1 |   | 4/2002 | Philippe et al. |
| 6,423,854 | B1 |   | 7/2002 | Philippe et al. |
| 6,733,785 | B1 | * | 5/2004 | Nakahara et al. ............ 424/484 |
| 2001/0002396 | A1 | * | 5/2001 | Achkar ....................... 514/167 |
| 2004/0167215 | A1 | * | 8/2004 | DeLuca et al. ............... 514/529 |
| 2004/0254245 | A1 | * | 12/2004 | Lintner ....................... 514/560 |
| 2010/0168045 | A1 | * | 7/2010 | Bordat et al. ................. 514/35 |

FOREIGN PATENT DOCUMENTS

| JP | 6-500079 A | 1/1994 |
| JP | 2002-527356 A | 8/2002 |
| JP | 2004-509073 A | 3/2004 |
| JP | 2004-123684 A | 4/2004 |
| JP | 2009-519298 | 5/2009 |
| WO | WO-82/02833 A1 | 9/1982 |
| WO | WO-92/04432 A1 | 3/1992 |
| WO | WO 93/00085 | 1/1993 |
| WO | WO-99/10318 A1 | 3/1999 |
| WO | WO-99/32077 A1 | 7/1999 |
| WO | WO 00/03700 | 1/2000 |
| WO | WO-00/03700 A1 | 1/2000 |
| WO | WO-01/66077 A | 9/2001 |
| WO | WO-01/66077 A1 * | 9/2001 |
| WO | 02/03912 A2 | 1/2002 |

OTHER PUBLICATIONS

Bessou et al., "Use of Human Skin Reconstructs in the Study of Pigment Modifiers", Arch Dermatol, vol. 133, pp. 331-336, Mar. 1997.

* cited by examiner

*Primary Examiner* — Ali Soroush
(74) *Attorney, Agent, or Firm* — Birch, Stewart, Kolasch & Birch, LLP

(57) ABSTRACT

The invention concerns the cosmetic or dermatological use of at least one compound of formula (I), wherein: $R_1, R_2, R_3, R_4, R_5$ and G are such as defined in the description as whitening and/or depigmenting agents for the skin and/or hairs and/or the hair. The invention also concerns a cosmetic method for whitening and/or lightening the skin and/or hairs and/or the hair comprising applying a composition of the invention.

8 Claims, 5 Drawing Sheets

Melanin dose-response and MTT of B16 melanocytes with oxoretinoids

Melanin dose-response and MTT of B16 melanocytes with oxoretinoids

Melanin dose-response and MTT of B16 melanocytes with oxoretinoids

USE OF POLYUNSATURATED COMPOUNDS AS WHITENING AGENTS

This invention relates to the cosmetic and/or dermatological use of polyunsaturated compounds as whitening agents for the skin and/or bodily hair and/or the hair on the head.

Retinoic derivatives are used today in dermatology in different indications, such as psoriasis or ichthyosis or even to obtain a depigmentation of the skin (reduction of melanogenesis under the action of vitamin A).

However, the use of retinoic derivatives by topical route encounters a certain number of difficulties owing a lack of stability of these derivatives over time and in the presence of light, irritation resulting from local concentrations and low penetration of these derivatives through the corneal layer. This latter disadvantage is due to the considerable lipophilia of the substance which, deposited on the skin, is in fact extensively eliminated with desquamation.

Secondary effects, redness, irritation, oedema and excessive desquamation limit the use of these retinoic derivatives to patients who are genuinely motivated.

Hence the interest in improving the bio-availability of the agent and its penetration, while avoiding the harmful effects of local over-concentrations.

The Applicant has shown that, in a surprising manner, certain polyunsaturated derivatives have properties which inhibit the production of melanin by melanocytes, thus demonstrating their interest in the cosmetic and/or dermatological domain.

These compounds are characterised by a cyclohexenic structure replaced by various radicals, including an oxygenated functional grouping, and a polyunsaturated radical. In particular, the derivatives used in connection with the invention are related to retinoids.

These derivatives are known and described in particular for their pharmaceutical properties, more particularly in the field of anticarcinogenics.

We shall mention, for example, the patent application WO 00/03700, which describes compounds containing oxo retinoids in the treatment of abnormal cell proliferation, and the document WO 92/04432, which describes the use of oxo retinoids in cancer treatment.

In the cosmetological field, the application WO/02833 describes the use of retinoids to increase the rate at which hair grows and the application WO 01/66077 describes the cosmetic use of oxo retinoid derivatives in the treatment of skin disorders such as acne, keratoses and rosacea.

Figure 1:
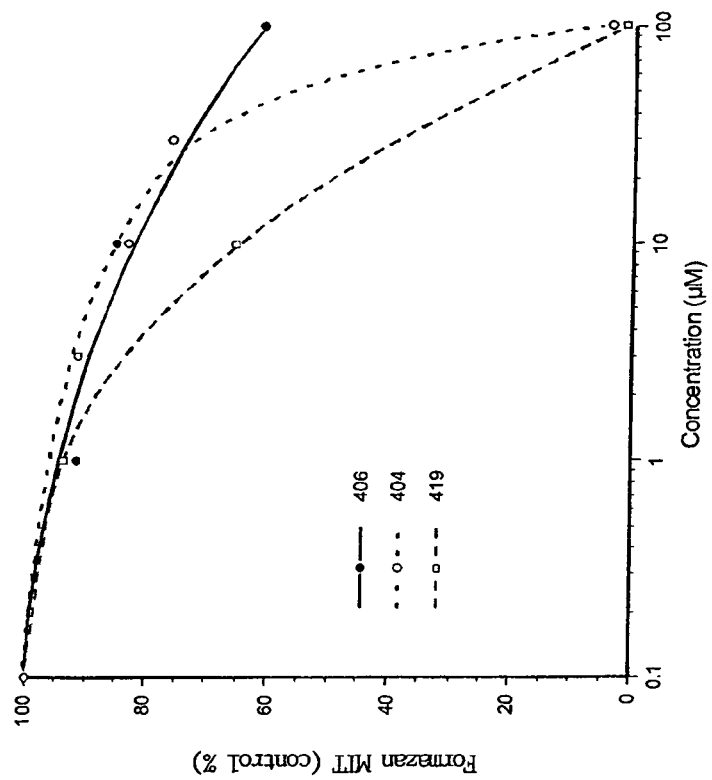
FIGS. 1 and 2 show the toxicity of retinoids with BDV II keratinocytes and present the viability of cells to concentration.
Figure 1:
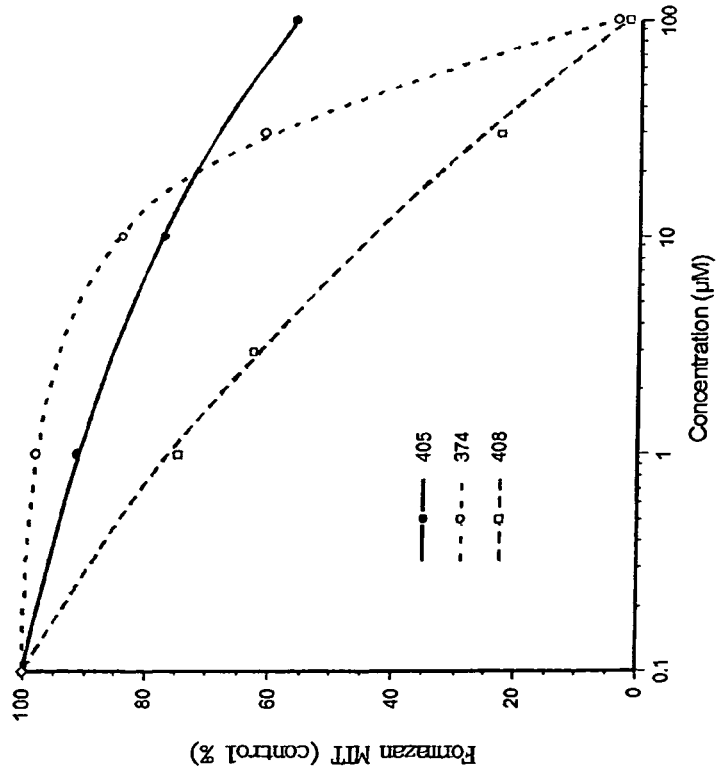

Accordingly, this invention relates to the cosmetic use of at least one compound with the formula

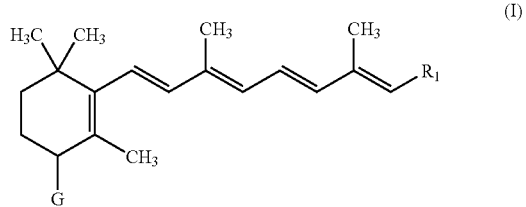

in which

R1 represents a $R'_1$ or $-A-R'_1$ grouping, in which $R'_1$ is chosen from —COOH, —COOR$_3$, —OCOR$_3$, —CONH$_2$, —CONHR$_3$, —CONR$_3$R$_4$, —CHO, —CH$_2$OR$_5$ and A represents a linear or ramified C$_1$-C$_{16}$ alkylene grouping, a linear or ramified C$_2$-C$_{16}$ alkenylene grouping, or a linear or ramified C$_2$-C$_{16}$ alkynylene grouping, G forms with the carbon to which it is attached a C=O grouping, or represents an —OH, —OR$_2$ or —OCOR$_2$ grouping, R$_2$ represents a sometimes replaced linear or ramified C$_1$-C$_{16}$ alkyl grouping, a sometimes replaced linear or ramified C$_2$-C$_{16}$ alkenyl grouping, a sometimes replaced linear or ramified C$_2$-C$_{16}$ alkynyl grouping or a linear or ramified acyl (C$_2$-C$_{16}$), R3 and R4 represent independently a sometimes replaced linear or ramified C$_1$-C$_{16}$ alkyl radical, a sometimes replaced linear or ramified C$_2$-C$_{16}$ alkenyl radical, a sometimes replaced linear or ramified C$_2$-C$_{16}$ alkynyl radical, R5 represents a sometimes replaced linear or ramified C$_1$-C$_{16}$ alkyl radical, a sometimes replaced linear or ramified C$_2$-C$_{16}$ alkenyl radical, a sometimes replaced linear or ramified C$_2$-C$_{16}$ alkynyl radical or a linear or ramified C$_2$-C$_{16}$ acyl, their enantiomers, diasterisomers, and their salts, if any, for addition to a physiologically acceptable acid or base, in a composition, as a skin whitening and/or bleaching agent for the skin, body hairs or hair of the head.

The invention relates also to the use of at least one compound with the formula (I) as defined above, for the manufacture of a dermatological composition intended to remove pigment from human skin.

Among acids that are pharmaceutically acceptable, we can mention in a non-limiting manner hydrochloric, hydrobromic, sulphuric, phosphonic, acetic, trifluoroacetic, lactic, pyruvic, malonic, succinic, glutaric, fumaric, tartaric, maleic, methanesulphonic, camphoric, oxalic acids, etc.

Among bases that are pharmaceutically acceptable, we can mention in a non-limiting manner sodium hydroxide, potassium hydroxide, triethylamine, tert-butylamine, etc.

Double links of the unsaturated design are in general all of configuration E, but this invention relates also to the use of compounds of formula (I) for which all or a part only of the double links has a configuration Z.

The termination "-ene" means that the grouping in question is a bivalent radical having the same design as the basic radical, both in the most general aspect of this invention and in particular aspects, advantageous and/or preferred.

The expression "sometimes replaced" associated with alkyl, alkenyl and alkynyl groupings means that these groupings are sometimes replaced by a number of halogen atoms or a linear or ramified alkoxy (C$_1$-C$_{16}$), a hydroxy, linear or ramified tri-alkyl-sillyle (C$_3$-C$_{18}$), mercapto, alkylthio, cyano, amino (sometimes replaced by one or two linear or ramified alkyl (C$_1$-C$_{16}$) groupings), nitro, carboxy, formyl, alkoxycarbonyl, aminocarbonyl (sometimes replaced by one or two linear or ramified alkyl (C$_1$-C$_{16}$) groupings), and carbamoyl groupings.

The alkyl radicals present in formula (I) compounds used according to the invention are more preferably linear or ramified (C$_1$-C$_6$) alkyl radicals. We can cite in particular the methyl, ethyl, propyl, iso-propyl, butyl, sec-butyl, tert-butyl, pentyl, isopentyl and hexyl groupings.

The alkenyl radicals present in formula (I) compounds used according to the invention will be advantageously linear or ramified (C$_2$-C$_6$) alkenyl radicals; we can for example cite the allyl or vinyl groupings.

The alkynyl radicals present in formula (I) compounds used according to the invention will be advantageously linear or ramified ($C_2$-$C_6$) alkynyl radicals; we can for example cite the alcyne, propyne and butyne groupings.

In the formula (I) compounds used, the $R_1$ grouping represents advantageously a $R'_1$ grouping chosen from —COOH, —COOR$_3$, —CHO, in which $R_3$ is as defined earlier.

Formula (I) compounds particularly suited to use in connection with this invention are those for which G forms with the carbon to which it is attached a C=O grouping, or represents an —OH grouping, or even an —O—CO-methyl grouping.

According to one particular characteristic of the invention, we shall more particularly use compounds of the general formula (I) defined earlier, in which A represents a methylene grouping.

According to an additional characteristic of the invention, compounds of general formula (I) are used in a composition stabilised by the presence of at least one liposoluble antioxidant as described in French patent application 2 718 021, and in particular nordihydroguaiaretic acid.

More particularly, formula (I) compounds used for the implementation of this invention will be chosen from the following compounds:

The tert-butylic ester of (2E,4E,6E,8E)-3,7-dimethly-9-(2,6,6-trimethyl-3-oxo-cyclohex-1-enyl) 2,4,6,8-tetraenoic acid,

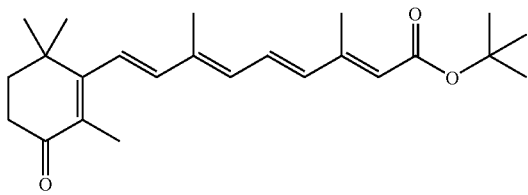 [SMILES: CC1=C(/C=C/C(C)=C/C=C/C(C)=C/C(=O)OC(C)(C)C)C(C)(C)CCC1=O]

This invention relates also to the compound above in this capacity the tert-butylic ester of (2E,4E,6E, 8E)-9-(3-hydroxy-2,6,6-trimethyl-cyclohex-1-enyl)-3,7-dimethyl-nona-2,4,6,8-tetraenoic acid,

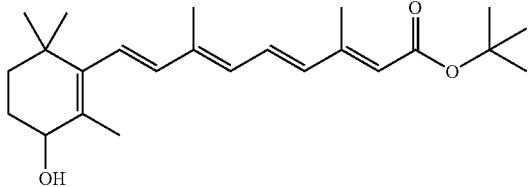 [SMILES: CC1=C(/C=C/C(C)=C/C=C/C(C)=C/C(=O)OC(C)(C)C)C(C)(C)CCC1O]

This invention relates also to the compound above in this capacity (2E,4E,6E,8E)-9-[3-(3-hydroxy)-2,6,6-trimethyl-cyclohex-1-enyl]-3,7-dimethyl-nona-2,4,6,8-tetraenal,

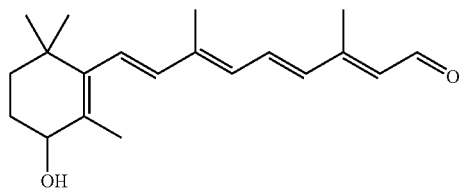 [SMILES: CC1=C(/C=C/C(C)=C/C=C/C(C)=C/C=O)C(C)(C)CCC1O]

2E,4E,6E,8E)-9-[3-(3-oxo)-2,6,6-trimethyl-cyclohex-1-enyl]-3,7-dimethyl-nona-2,4,6,8-tetraenal,

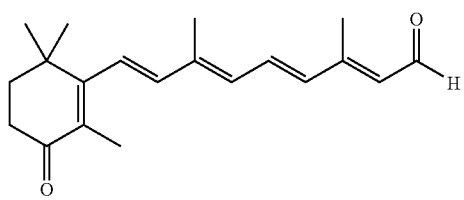 [SMILES: CC1=C(/C=C/C(C)=C/C=C/C(C)=C/C=O)C(C)(C)CCC1=O]

The methylic ester of (2E,4E,6E,8E)-9-[3-(3-oxo)-2,6,6-trimethyl-cyclohex-1-enyl]-3,7-dimethyl-nona-2,4,6,8-tetraenoic acid,

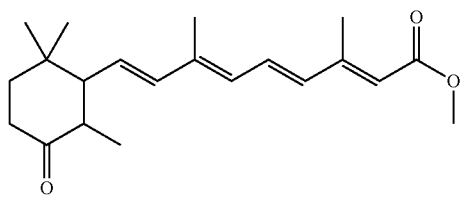 [SMILES: COC(=O)/C=C(C)/C=C/C=C(C)/C=C/C1C(C)C(=O)CCC1(C)C]

The methylic ester of (2E,4E,6E,8E)-9-[3-(3-hydroxy)-2,6,6-trimethyl-cyclohex-1-enyl]-3,7-dimethyl-nona-2,4,6,8-tetraenoic acid,

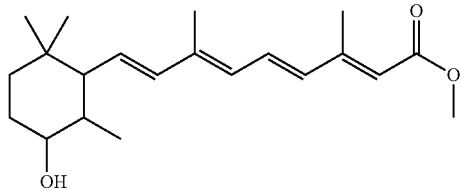 [SMILES: COC(=O)/C=C(C)/C=C/C=C(C)/C=C/C1C(C)C(O)CCC1(C)C]

(2E,4E,6E,8E)-9-[3-(3-hydroxy)-2,6,6-trimethyl-cyclohex-1-enyl]-3,7-dimethyl-nona-2,4,6,8-tetraenoic acid,

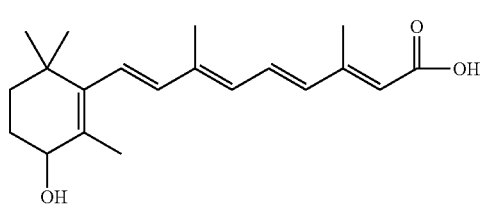 [SMILES: CC1=C(/C=C/C(C)=C/C=C/C(C)=C/C(=O)O)C(C)(C)CCC1O]

(2E,4E,6E,8E)-9-[3-(3-oxo)-2,6,6-trimethyl-cyclohex-1-enyl]-3,7-dimethyl-nona-2,4,6,8-tetraenyl acetate,

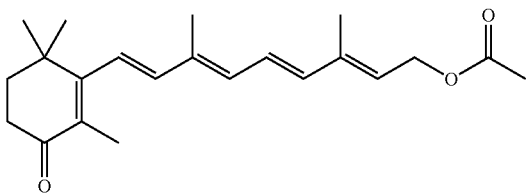 [SMILES: CC(=O)OC/C=C(C)/C=C/C=C(C)/C=C/C1=C(C)C(=O)CCC1(C)C]

the tert-butylic ester of (2E,4E,6E,8E)-9-[3-(3-acetoxy)-2,
6,6-trimethyl-cyclohex-1-enyl]-3,7-dimethyl-nona-2,4,
6,8-tetraenoic acid,

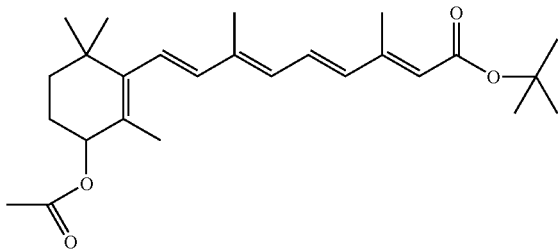 [SMILES: CC(=O)OC1CCC(C)(C)C(/C=C/C(C)=C/C=C/C(C)=C/C(=O)OC(C)(C)C)=C1C]

This invention relates also to the above compound in that capacity.

The formula (I) compounds according to this invention are familiar or well prepared by methods of operation familiar from commercial reagents and products.

Formula (I) compounds have the advantage of being only marginally toxic, and have demonstrated good properties inhibiting the production of melanin by melanocytes. They also have less marked secondary effects (dryness of the skin and inflammation) than the reference products used currently, such as retinoic acids or other synthetic acids of the same type. Their stability has also been improved.

This invention accordingly relates also to a cosmetic method for whitening and/or bleaching the skin and/or the body hairs and/or the hair of the head, comprising the application to the skin and/or the body hairs and/or the hair of the head of a composition containing at least one (I) formula compound as defined in claim 1.

The invention relates also to a cosmetic method for eliminating brownish pigment marks and/or marks of ageing of human skin, comprising the application to the skin of a cosmetic composition containing at least one (I) formula compound as defined earlier.

Compounds according to the invention, alone or mixed, as well as the composition comprising them, can be used as a topical application to the skin, body hair or hair of the head.

The quantity of compounds to be used in the context of the invention quite clearly depends on the desired effect.

For example, this quantity can vary, for example, from 0.01% to 5% by weight and preferably from 0.05% to 0.5% by weight, relative to the total weight of the composition.

The composition according to the invention is intended particularly for a topical application; it comprises also a physiologically acceptable medium, i.e. compatible with the skin, including where relevant the scalp, mucous membranes, the hair of the head, body hair and/or the eyes.

The composition can also comprise all the constituents usually employed in the application considered. We can specifically cite water, solvents, mineral, animal or vegetable oils, waxes, pigments, charges, tension-agents, cosmetic or dermatological agents, UV filters, polymers, gelling agents and preservatives.

If the composition of the invention is an emulsion, the proportion of the fatty phase can vary from 5 to 80% by weight, and more preferably from 5 to 50% by weight relative to the total weight of the composition. Oils, emulsifiers and any co-emulsifiers used in the composition in the form of an emulsion are chosen from those conventionally used in the field in question. The emulsifier and the co-emulsifier are present, in the composition, in a proportion that can vary from 0.3 to 30% by weight, and more preferably from 0.5 to 20% by weight relative to the total weight of the composition.

Certainly those skilled in the art will take care to choose this or these potential complementary compounds, and/or their quantity, in a manner such that the advantageous properties of compounds according to the invention would not be altered or altered substantially by the addition considered.

The composition according to the invention can occur in all the galenic forms used normally in the cosmetic and dermatological domains; this may be particularly in the form of an aqueous, hydro-alcoholic, sometimes gelled solution, a dispersion of the lotion type, sometimes having two phases, an oil-in-water or water-in-oil or multiple emulsion, an aqueous gel and can have the appearance of a cream, a pomade, a paste or a foam. It can also be applied to the skin or the hair of the head in the form of an aerosol. It can be used in the form of a care product, as well as during or after shampooing.

In one advantageous appearance, the compositions used in connection with this invention also contain at least one other whitening and/or depigmenting agent. We can cite, for example, kojic acid, ellagic acid, arbutin and its derivatives, hydroquinone, aminophenol derivatives such as those described in the WO 99/10318 and WO 99/32077 applications, L-2-oxothiazolidine-4-carboxylic acid or procystein, as well as its salts and esters, ascorbic acid and its derivatives, 4-butyl-resorcinol or lucinol, thiourea and its derivatives, D-pantethein calcium sulphonate; and plant extracts, in particular bearberry, liquorice, mulberry and skullcap, without this list being limitative.

In another appearance of the invention, the compositions used can also include at least one desquamant agent, and/or at least one soothing agent, and/or at least one organic photoprotector agent and/or at least one inorganic photoprotector agent.

Among the desquamant agents used conventionally in cosmetics, we can cite for example β-hydroxyacids, in particular salicylic acid and its derivatives, α-hydroxyacids, such as glycolic, citric, lactic, tartaric, malic or mandelic acids, or urea.

Among soothing agents, we will mention for example Canola oil, bisabolol, camomile extracts, allantoin, oils unsaturated in omega 3, such as oils musk rose, black currant, ecchium, fish, aloe vera, phytosterols, cortisone, hydrocortisone, indomethacin and beta methasone.

The organic photoprotector agents used in connection with this invention will be chosen particularly from the anthranilates; cinnamic derivatives; dibenzoylmethane derivatives; salicylic derivatives, camphor derivatives; triazine derivatives, benzophenone derivatives;β,β-diphenylacrylate; benzotriazol derivatives; benzalmonate derivatives; imidazolines; bis-benzo-azolyle derivatives, p-aminobenzoic (PABA) derivatives; methylene bis-(hydroxyphenyl benzotriazol) derivatives.

The inorganic photoprotector agents are chosen from the pigments or even again from metallic oxide nanopigments (average size of the primary particles: generally between 5 nm and 100 nm, more preferably between 10 nm and 50 nm) sometimes coated for example with titanium oxide (amorphous or crystallised in the form of rutile and/or anatase), iron, zinc, zirconium or cerium nanopigments which are all UV photoprotector agents well known in their own right. Conventional coating agents are also alumina and/or aluminium stearate.

Photoprotector agents are generally present in the composition according to the invention in proportions varying from 5 to 20% by weight relative to the total weight of the composition, and more preferably varying from 10 to 15% by weight relative to the total weight of the composition.

The following examples illustrate the invention, but could not limit its scope.

EXAMPLE 1

2-trimethylsilanyl-ethyl ester of (2E,4E,6E, 8E)-3,7-dimethyl-9-(2,6,6-trimethyl-3-oxo-cyclohex-1-enyl)-nona-2,4,6,8-tetraenoic acid

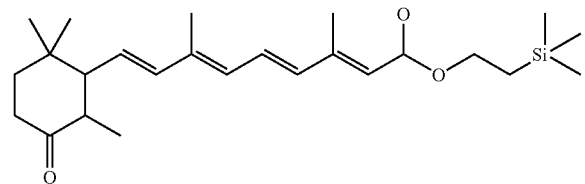 [SMILES: CC(/C=C/C1C(C)C(=O)CCC1(C)C)=C\C=C\C(C)=C\C(O)OCC[Si](C)(C)C]

22 g (55.0 mmol) of trimethylsylilethyl-retinate, obtained previously, are solubilised in 40 volumes of dichloromethane, under a flow of nitrogen and away from light. 329 g (3.78 mol) of manganese oxide are added and the mixture is agitated for 24 hours. The medium is filtered over celite, concentrated in vacuo. 25 g of unprocessed product are purified over a silica column, eluted by a heptane/ethyl acetate gradient in order to produce 14.3 g (34.5 mmol) of an orange solid.

Rf=0.5 (7/3 heptane/ethyl acetate)

EXAMPLE 2

2-trimethylsilanyl-ethyl ester of (2E,4E,6E, 8E)-9-(3-hydroxy-2,6,6-trimethyl-cyclohex-1-enyl) 3,7-dimethyl-nona-2,4,6,8-tetraenoic acid

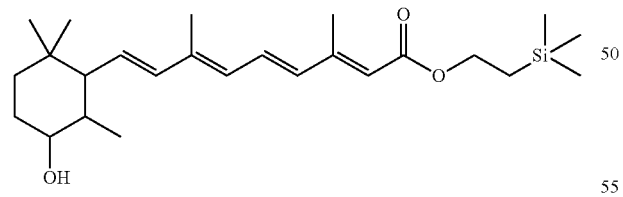

14.3 g (34.5 mmol) of the compound described in example 1 are solubilised in 10 volumes of tetrahydrofuran, under a flow of nitrogen and away from light. The medium is chilled to −78° C. and 29 ml (35.2 mmol) of a 20% solution of Dibal-H in toluene are added drop-by-drop, while controlling the temperature at −78° C. The medium is agitated for 5 hours. 20 volumes of a saturated solution of Rozen salts are added slowly at −78° C. The medium is extracted to ethyl acetate. The organic phases are washed with a saturated solution of NaCl, dried over MgSO$_4$ and concentrated in vacuo. 16 g of unprocessed product are purified over a silica column, eluted by a heptane/ethyl acetate gradient to produce 10 g (24.0 mmol) of a yellow solid.

Rf=0.4 (7/3 heptane/ethyl acetate)

EXAMPLE 3

Step 1 tert-butylic ester of (2E,4E,6E,8E)-3,7-dimethyl-9-(2,6,6-trimethyl-cyclohex-1-enyl)-nona-2,4,6,8-tetraenoic acid

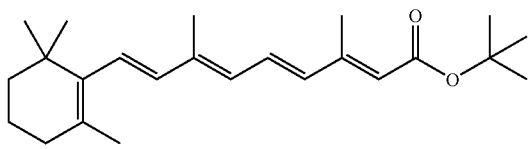 [SMILES: CC1=C(/C=C/C(C)=C/C=C/C(C)=C/C(=O)OC(C)(C)C)C(C)(C)CCC1]

9.1 g (30.3 mmol) of retinoic acid are solubilised in 10 volumes of dichloromethane. At room temperature, under a flow of nitrogen and away from light, 14 g (69.6 mmol) of 2-tert-butyl-1,3-diisopropyl-isourea are added. The medium is agitated for 18 hours. Thin layer chromatography monitoring reveals the end of the reaction (UV revelation). The urea salts are then filtered, the filtrate is concentrated away from light and purified over a silica column, with 9/1 heptane/ethyl acetate for the elutent, away from light, to produce 10.4 g (29.2 mmol) of a pasty oil.

Rf=0.4 (8/2 heptane/ethyl acetate)

Step 2 tert-butylic ester of (2E,4E,6E,8E)-3,7-dimethyl-9-(2,6,6-trimethyl-3-oxo-cyclohex-1-enyl)-nona-2,4,6, 8-tetraenoic acid

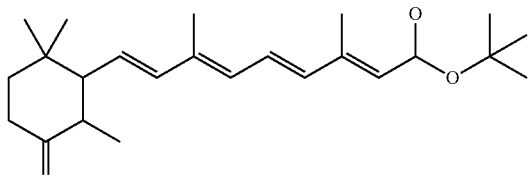

10.4 g (29.2 mmol) of the compound from step 1 are solubilised in 40 volumes of dichloromethane, under a flow of nitrogen and away from light. 114 g (131 mmoll) of manganese oxide are added and the mixture is agitated for 72 hours. The medium is filtered over celite, concentrated in vacuo and purified over a silica column by a 9/1 heptane/ethyl acetate mixture. After crystallisation, 10 g (27.0 mmol) of orange solid are obtained.

Rf=0.5 (7/3 heptane/ethyl acetate)

EXAMPLE 4 tert-butylic ester of (2E,4E,6E,8E)-9-(3-hydroxy-2,6,6-trimethyl-cyclohex-1-enyl)-3,7-dimethyl-nona-2,4,6,8-tetraenoic acid

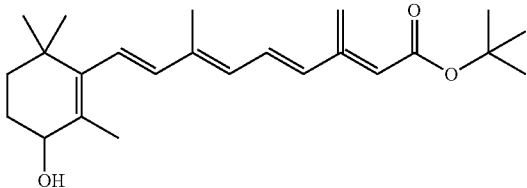

10 g (27.0 mmol) of the compound from example 3 are solubilised in 10 volumes of tetrahydrofuran, under a flow of nitrogen and away from light. The medium is chilled to −78° C. and 23 ml (27.5 mmol) of a 20% solution of Dibal-H in toluene are added drop by drop while controlling the temperature at −78° C. The medium is agitated for 3 hours. At −60° C., 20 volumes of a saturated solution of Rozen salts are added. The medium is extracted to dichloromethane. The organic phases are washed with a saturated solution of NaCl, dried over MgSO$_4$, and concentrated in vacuo. 15 g of the unprocessed product are purified over a silica column, eluted by a heptane/ethyl acetate gradient to produce 6.8 g (18.3 mmol) of a pasty yellow oil.

Rf=0.3 (7/3 heptane/ethyl acetate)

EXAMPLE 5

Methylic ester of (2E,4E,6E,8E)-9-[3-(3-oxo)-2,6,6-trimethyl-cyclohex-1-enyl]-3,7-dimethyl-nona-2,4,6,8-tetraenoic acid

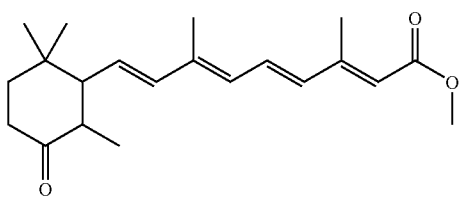 [SMILES: COC(=O)/C=C(C)/C=C/C=C(C)/C=C/C1C(C)C(=O)CCC1(C)C]

1 g (0.07 mol) of retinoic acid are placed in suspension in 12 volumes of methyl alcohol, under a flow of nitrogen and away from light. The medium is corrected to 15° C. and 125 ml (0.28 mol) of a solution of 2M trimethylsilyldiazomethane in hexane are added with care drop by drop. The medium is corrected to room temperature, under agitation, during one night. The medium is hydrolysed by 2 volumes of water and then concentrated in vacuo. The residue is transferred into ethyl acetate, washed with water and then with a saturated solution of NaCl. The organic phase is dried over MgSO4, then concentrated in vacuo. 22 g of a yellow pasty oil is obtained (100%) and then committed without any additional purification.

16.8 g (53.4 mmol) of this oil are placed in solution in 40 volumes of dichloromethane, under a flow of nitrogen and away from light. 69.7 g (0.80 mol) of manganese oxide are added to the medium, which is agitated for 48 hours. The mixture is filtered over celite and the filtrate is concentrated in vacuo in order to produce the required product.

Rf=0.2 (9/1 heptane/ethyl acetate)

EXAMPLE 6

Methylic ester of (2E,4E,6E,8E)-9-[3-(3-hydroxy)-2,6,6-trimethyl-cyclohex-1-enyl]-3,7-dimethyl-nona-2,4,6,8-tetraenoic acid

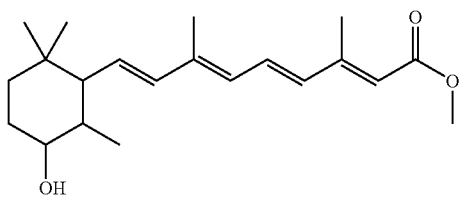 [SMILES: COC(=O)/C=C(C)/C=C/C=C(C)/C=C/C1C(C)C(O)CCC1(C)C]

4 g (0.012 mol) of the compound from example 5 are dissolved in 10 volumes of tetrahydrofuran, under a flow of nitrogen and away from light. The medium is chilled to −78° C. and 17 ml (0.017 mol) of a solution of 1M Dibal-H in dichloromethane are added drop by drop while controlling the temperature at −78° C. The medium is agitated for 1 hour. At −60° C., 30 volumes of a saturated solution of Rozen salts are added. The medium is extracted to ethyl acetate. The organic phases are washed with a saturated solution of NaCl, washed over MgSO$_4$, and concentrated in vacuo. 3.94 g of unprocessed product are obtained and purified over a silica column eluted by an 8/2 heptane/ethyl acetate system to produce the required product.

Rf=0.2 (8/2 heptane/ethyl acetate)

EXAMPLE 7

(2E,4E,6E,8E)-9-[3-(3-hydroxy)-2,6,6-trimethyl-cyclohex-1-enyl]-3,7-dimethyl-nona-2,4,6,8-tetraenoic acid

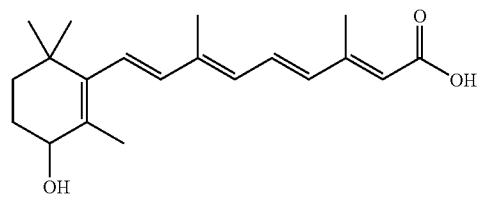 [SMILES: CC1=C(/C=C/C(C)=C/C=C/C(C)=C/C(=O)O)C(C)(C)CCC1O]

0.9 g (2.70 mmol) of the compound described in example 6 are solubilised in 9 volumes of methyl alcohol and 4 volumes of water. 250 mg (5.9 mmol) of a 56% LiOH solution in water are added at room temperature. After 4 days of agitation, the reagent medium is concentrated in vacuo, the remaining aqueous phase is extracted to ethyl acetate, then acidified to pH 5 by a 3M HCl solution and extracted again by ethyl acetate. The organic phases are dried over MgSO4, then concentrated in vacuo and produce the required product.

Rf=0.05 (8/2 heptane/ethyl acetate)

EXAMPLE 8 tert-butylic ester of (2E,4E,6E,8E)-9-[3-(3-acetoxy)-2,6,6-trimethyl-cyclohex-1-enyl]-3,7-dimethyl-nona-2,4,6,8-tetraenoic acid

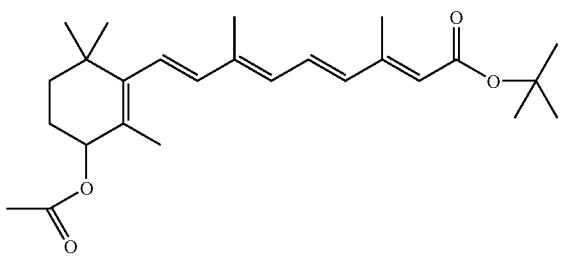 [SMILES: CC(=O)OC1CCC(C)(C)C(/C=C/C(C)=C/C=C/C(C)=C/C(=O)OC(C)(C)C)=C1C]

2 g (5.4 mmol) of the compound from example 4 are dissolved in 10 volumes of tetrahydrofuran, away from light. At 5° C., under a flow of nitrogen, 1.62 g of acetic anhydride (16.2 mmol), 0.65 g of triethylaminine (6.5 mmol) and 849 mg (10.8 mmol) of pyridine are added. The medium is corrected to room temperature and agitated for 20 hours away from light. Once the reaction has ended, the reagent medium is concentrated and then purified over a silica column eluted by a 9/1 heptane/ethyl acetate system to produce the required product.

Rf=0.6 (9/1 heptane/ethyl acetate)

EXAMPLE 9

(2E,4E,6E,8E)-9-[3-(3-oxo)-2,6,6-trimethyl-cyclohex-1-enyl]-3,7-dimethyl-nona-2,4,6,8-tetraenal

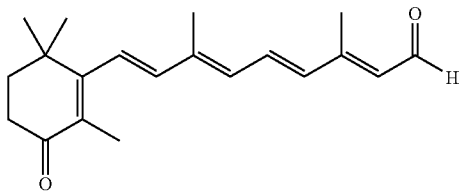 [SMILES: CC1=C(/C=C/C(C)=C/C=C/C(C)=C/C=O)C(C)(C)CCC1=O]

1 g (3.5 mmol) of Retinal is dissolved in 45 volumes of dichloromethane. Away from light, 23 g (0.265 mol) of manganese oxide are added to the medium, which is agitated at room temperature for 4 days. After filtration over celite and washes of the solid in dichloromethane, the filtrates are concentrated in vacuo. The residue is purified over a silica column, eluted buy a 98/2 heptane/ethyl acetate system. The solid is recrystallised in the heptane to produce the required product.

Rf=0.3 (7/3 heptane/ethyl acetate)

Mass spectrometry: [MNa$^+$] 321 ([MH$^+$] calculated 298)

EXAMPLE 10

(2E,4E,6E,8E)-9-[3-(3-hydroxy)-2,6,6-trimethyl-cyclohex-1-enyl]-3,7-dimethyl-nona-2,4,6,8-tetraenal

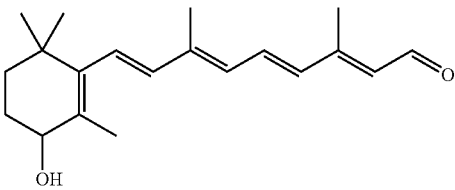 [SMILES: CC1=C(/C=C/C(C)=C/C=C/C(C)=C/C=O)C(C)(C)CCC1O]

2 g (5.37 mmol) of the compound from example 4 are placed in solution in 10 volumes of toluene, under a flow of nitrogen and away from light. The medium is chilled to −78° C., then 4.57 ml (5.48 mmol) of a 20% Dibal-H solution in toluene are added drop-by-drop. After 3 hours of agitation at −78° C., 20 volumes of a saturated solution of Rozen salts are added. The medium is extracted to toluene, the organic phases are washed with a saturated solution of NaCl, dried over MgSO4, filtered and concentrated in vacuo. The unprocessed product obtained is purified over a silica column, eluted by a heptane gradient, 9/1 heptane/ethyl acetate, to produce the required component.

Rf=0.2 (7/3 heptane/ethyl acetate)

Mass spectrometry: [M+Na$^+$] 323 ([MH$^+$] calculated 300)

EXAMPLE 11

(2E,4E,6E,8E)-9-[3-(3-oxo)-2,6,6-trimethyl-cyclohex-1-enyl]-3,7-dimethyl-nona-2,4,6,8-tetraenyl acetate

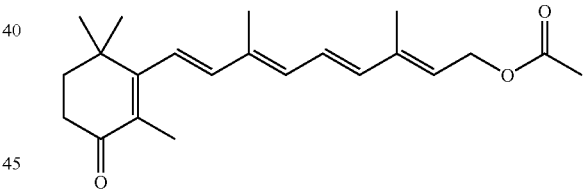

EXAMPLE 12

Toxicity Study

The objective of these tests is to measure the toxicity of the new retinoids on keratinocyte and melanocyte cells.

The method used is a cellular respiration test with the MTT (thiazolile blue) in order to assess cells that are still living.

Operating Protocol:

The MTT test gives a cellular respiration index; this involves a substrate of dehydrogenases in general and dehydrogenase succinate in particular. The MTT, yellow, partially soluble in water, is reduced in a violet compound, insoluble in water, but soluble in organic solvents (DMSO).

Prepare a 12 mM solution (5 mg/ml) of MTT in water or the culture medium.

Dilute this solution to 1:10 in the supernatant fluid or suspension of cells (final MTT 1.2 mM or 0.5 mg/ml), then leave to incubate for 3 hours at 37° C.

Aspirate the supernatant fluid, the dissolve the violet crystals of formazan MTT in DMSO.

Read the optical density of the solution at 550 nm (dilute beforehand as required).

Calibration line: MTT formazan 0-200 µM.

Figure 2:
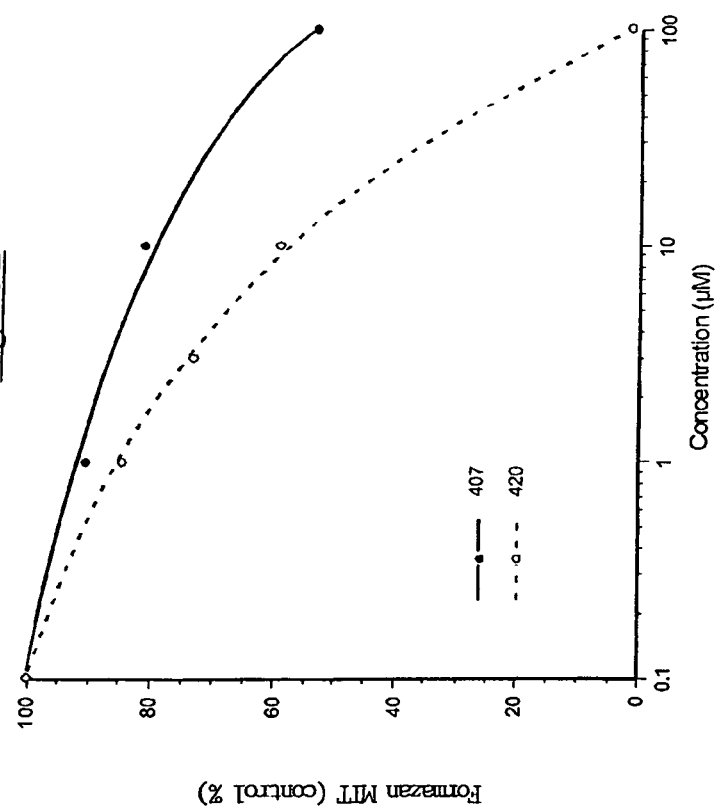

Results:

—On BDV II Keratinocytes:

These results are grouped in table no. 1 below "Toxicity of retinoids on BDV II keratinocytes" and in FIGS. 1 and 2, which represent the viability of cells according to concentration. The least toxic components are those of examples 7 and 8, followed by examples 3 and 4, then examples 5 and 6.

TABLE 1

BDV II murine keratinocytes

| Retinoid | Name | Concentration (µM) | % MTT | - IC 50 MTT (µM) |
|---|---|---|---|---|
| RA | Retinoic acid | 10 | 40 | 3 |
| 374 Ex 3 | tert-butyl 4-oxoretinoate | 10 | 85 | 60 |
| 404 Ex 4 | tert-butyl 4-hydroxyretinoate | 10 | 84 | 70 |
| 405 | 4-oxoretinoic acid | 10 | 78 | >100 |
| 406 Ex 7 | 4-hydroxyretinoic acid | 10 | 86 | >100 |
| 407 Ex 8 | tert-butyl 4-acetoxyretinoate | 10 | 82 | >100 |
| 408 Ex 5 | methyl 4-oxoretinoate | 10 | 59 | 15 |
| 419 Ex 6 | methyl 4-hydroxyretinoate | 10 | 66 | 30 |
| 420 Ex 11 | 4-oxoretinol acetate | 10 | 60 | 30 |

—On B16 Melanocytes:

These results are grouped in table no. 2 below "Toxicity of B16 murine melanocytes" and in the graphs on the left of FIGS. 3 to 5, which represent cell viability according to concentration. We can note that the least toxic compounds are those from example 6 and, to a marginally lower degree those from examples 8, 5, 3 and 4.

TABLE 2

B16 murine melanocytes

| Retinoid | Name | Concentration (µM) | % MTT | - IC 50 MTT (µM) |
|---|---|---|---|---|
| RA | Retinoic acid | 10 | 50 | 10 |
| 374 Ex 3 | tert-butyl 4-oxoretinoate | 10 | 80 | 30 |
| 404 Ex 4 | tert-butyl 4-hydroxyretinoate | 10 | 62 | 20 |
| 405 | 4-oxoretinoic acid | 10 | 76 | >100 |
| 406 Ex 7 | 4-hydroxyretinoic acid | 10 | 69 | 35 |
| 407 Ex 8 | tert-butyl 4-acetoxyretinoate | 10 | 82 | 60 |
| 408 Ex 5 | methyl 4-oxoretinoate | 10 | 86 | 60 |
| 419 Ex 6 | methyl 4-hydroxyretinoate | 10 | 93 | 70 |
| 420 Ex 11 | 4-oxoretinol acetate | 10 | 86 | 70 |

EXAMPLE 13

Study of Depigmenting Activity

The objective of these tests is to measure the depigmenting activity of new retinoids according to their concentration.

Operating Protocol:

The melanin is dosed according to the method described by S. Besson et al., Dermatology Archives. 133:331-336 (1997)'.

Reagents

Digestion plug: 100 mM NaCl, to mm-Tri-HCl, 1% SDS, 50 mM EDTA, pH 8.

For 50 ml: 292 mg NaCl, 299 mg tris acid, 73 mg tris base, 931 mg EDTA disodium dehydrate, 500 mg SDS, adjust pH ($\approx$5.5) to 8.0 with concentrated NaOH.

K proteinase 10 mg/ml in the digestion plug.

Procedure:

Calibration Line:

Prepare tubes containing synthetic melanin at concentrations of between 2.5 and 80 µg/ml in the DMSO.

Samples:

For the cells, determine the protein concentration beforehand, centrifuge in 2 ml tubes and remove the supernatant.

In 2 ml tubes containing a cell remainder, add 300 µl of digestion buffer and 3 µl of K proteinase.

Incubate for 2 hours at 50° C., then a night at 37° C.

Top up the volume to 1 ml with water, then sound test.

Centrifuge for 10 minutes at 20,000 g, drain off all the supernatant (clear) then dissolve the dry melanin remainder in 500-1000 µl of DMSO.

Measure the absorbency at 375 nm and check the spectrum.

Figure 3:
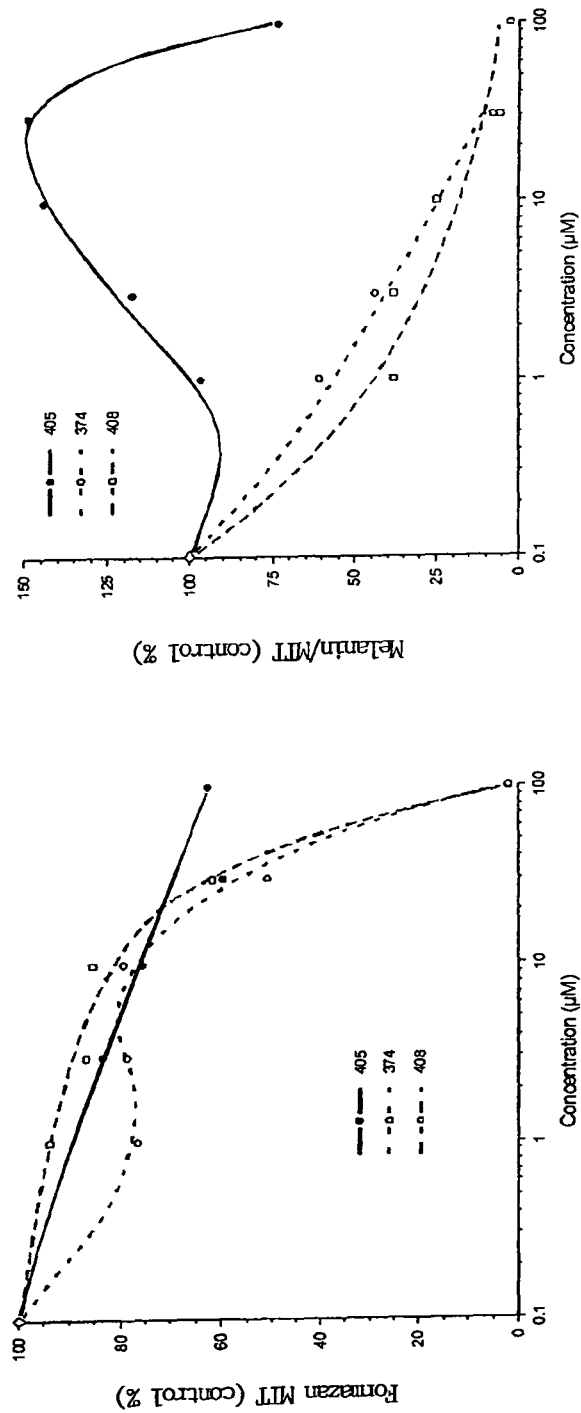
FIGS. 3-5 show the toxicity of retinoids with B16 murine melanocytes and present cell viability to concentration.
Figure 4:
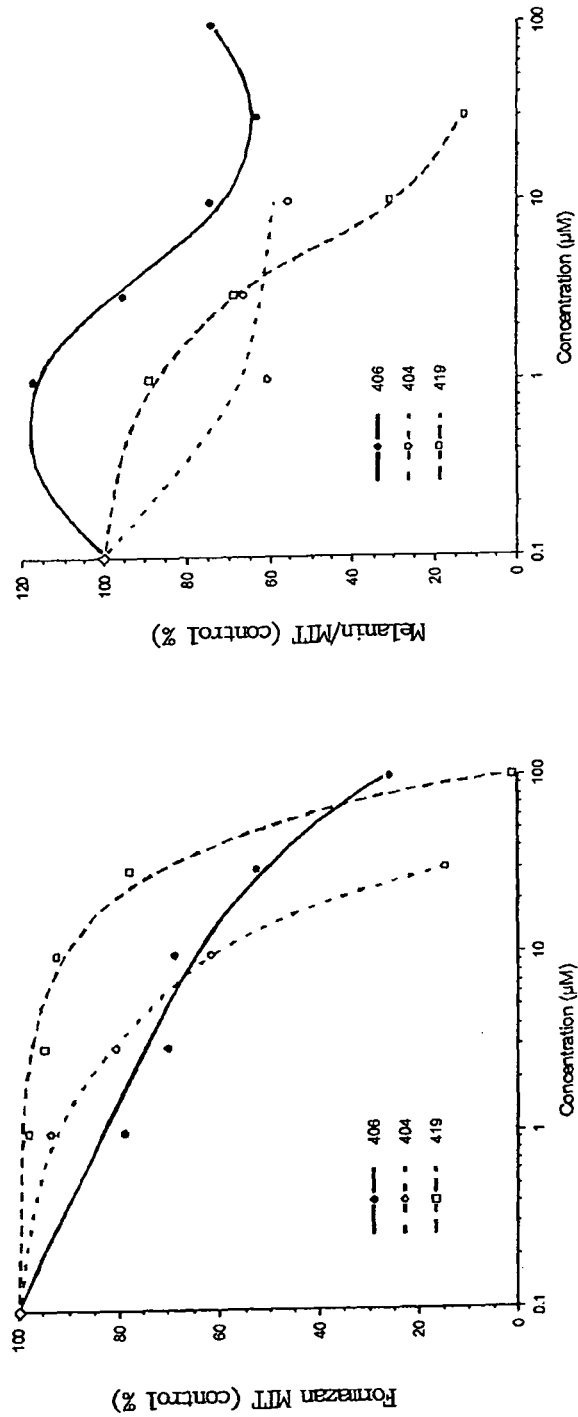
Figure 5:
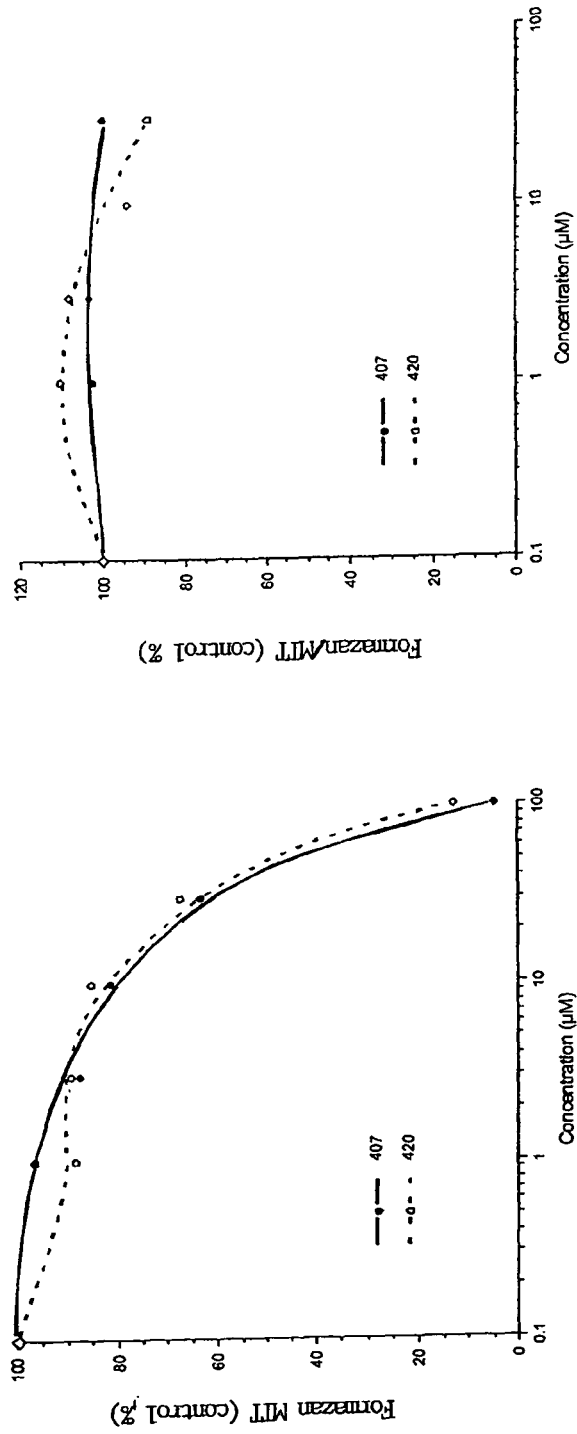

Results:

The melanin response doses are given in the graphs from the right part of FIGS. 3 to 5. These graphs represent the depigmenting activity of the product according to its concentration. By being placed at infratoxic doses, the net depigmenting efficacy promotes the compounds of examples 8, 3 and 5.

EXAMPLE 14

Whitening Composition

| Composition (H/E emulsion) | Quantity (g) |
|---|---|
| Example 9 compound | 0.1 |
| Vaseline | 8 |
| Glycerin 99.5% | 15 |
| Glyceryl stearate GS | 5 |
| Stearic acid | 3 |
| Liquid paraffin 352 | 4 |
| Cyclopentasiloxane | 3 |
| Magrogol 600 | 5 |
| Ethanolamine tri | 0.5 |
| Paraben | 0.4 |
| Purified water | QSP 100 |

Bleaching Lotion:

| Composition | Quantity (g) |
|---|---|
| Example 5 compound | 0.1 |
| B4F cocamido propyl | 2 |
| Macrogol 600 | 4 |
| Phenylethyl alcohol | 0.5 |
| Ethanolamine (tri) | 0.04 |
| Purified water | QSP 100 |

(Components are cited as chemical names or as CFTA names (International Cosmetic Dictionary and Handbook).

The invention claimed is:

1. A method for skin whitening and/or bleaching of the skin, body hairs and/or hair of the head, which comprises applying an effective amount of a composition to the skin and/or body hair and/or the hair of the head, wherein the composition comprises:
- (a) at least one compound of tert-butylic ester of (2E,4E, 6E,8E)-9-[3-(3-acetoxy)-2,6,6-trimethyl-cyclohex-1-enyl]-3,7-dimethyl-nona-2,4,6,8-tetraenoic acid, enantiomers, diasterisomers, and pharmaceutically acceptable salts thereof; and
- (b) at least one other whitening or depigmenting agent.

2. The method according to claim 1, which is for depigmenting human skin.

3. The method according to claim 1, wherein the quantity of the at least one compound is between 0.01% and 5% inclusive by weight relative to the total weight of the composition.

4. The method according to claim 1, wherein the composition further comprises at least one desquamant agent.

5. The method according to claim 1, wherein the composition further comprises at least one organic photoprotector agent and/or at least one inorganic photoprotector agent.

6. The method according to claim 1, wherein the composition further comprises at least one liposoluble antioxidant.

7. The method according to claim 6, wherein the liposoluble antioxidant is nordihydroguaiaretic acid.

8. The method according to claim 1, wherein brownish pigmentary marks and/or aging marks of the human skin are eliminated.

* * * * *